United States Patent [19]

Ullrich et al.

[11] Patent Number: 4,992,429
[45] Date of Patent: Feb. 12, 1991

[54] HMG-COA REDUCTASE INHIBITORS

[75] Inventors: John W. Ullrich, Audubon; Kent W. Neuenschwander, Ambler, both of Pa.; John R. Regan, Princeton, N.J.

[73] Assignee: Rhone-Poulenc Rorer Pharmaceuticals Inc., Fort Washington, Pa.

[21] Appl. No.: 398,015

[22] Filed: Aug. 24, 1989

[51] Int. Cl.$^5$ .............. A61K 31/66; C07D 9/30; C07D 9/32
[52] U.S. Cl. .............. 514/129; 514/114; 514/128; 514/130; 549/563; 556/405; 558/169; 558/177; 560/9; 560/11; 560/12; 560/13; 560/14; 560/45; 560/59; 562/11; 562/23
[58] Field of Search .............. 558/177, 169; 514/114, 514/128, 129, 130; 560/9, 11, 12, 13, 14, 45, 59; 562/11, 23

[56] References Cited

U.S. PATENT DOCUMENTS

| | | | |
|---|---|---|---|
| 4,268,507 | 5/1981 | Nguyen Mong | 514/130 |
| 4,282,155 | 8/1981 | Smith et al. | 549/292 |
| 4,567,289 | 1/1986 | Willard et al. | 560/59 |
| 4,611,067 | 9/1986 | Volante et al. | 558/405 |
| 4,668,699 | 5/1987 | Hoffman et al. | 514/824 |
| 4,681,893 | 7/1987 | Roth | 514/422 |
| 4,904,646 | 2/1990 | Karanewsky et al. | 514/120 |

OTHER PUBLICATIONS

Core et al., *J. Med. Chem.*, 12, pp. 334-336 (1969).

*Primary Examiner*—Mukund J. Shah
*Assistant Examiner*—Emily Bernhardt
*Attorney, Agent, or Firm*—Imre (Jim) Balogh; James A. Nicholson

[57] ABSTRACT

Disclosed are novel substituted cyclohexenyl phosphinylhydroxybutyrates as 3-hydroxy-3-methylglutaryl-coenzyme A reductase inhibitors useful as antihypercholesterolemic agents represented by the formula:

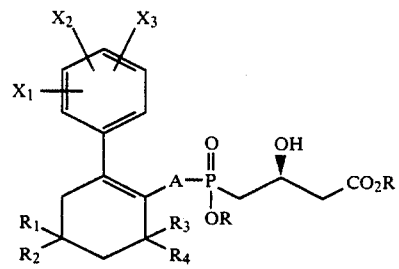

and pharmaceutically acceptable salts thereof.

19 Claims, No Drawings

HMG-COA REDUCTASE INHIBITORS

BACKGROUND OF THE INVENTION

1. Field of the Invention

The present invention relates to compounds, pharmaceutical compositions and a method useful for reducing serum cholesterol in humans. More particularly, the invention relates to substituted cyclohexenyl-phosphinyl-hydroxybutyrates and pharmaceutically acceptable salts thereof which are potent inhibitors of the enzyme 3-hydroxy-3-methylglutaryl-coenzyme A reductase (hereinafter HMG-CoA reductase), pharmaceutical compositions thereof, and a method of inhibiting biosynthesis of cholesterol for the treatment of atherosclerosis, hyperlipidemia and hypercholesterolemia.

2. Related Prior Art

Inhibitors of HMG-CoA are effective in lowering blood plasma cholesterol level as well as inhibiting the biosynthesis of cholesterol in humans. As such, inhibitors of HMG-CoA are useful in the prevention and treatment of coronary heart diseases. The prior art recognizes the importance of such compounds, e.g., Bethridge et al., Brit. Med. J., 4,500 (1975) and Brown et al., Scientific American, 58 Nov. (1984). Illustrative references directed to such compounds follow.

U.S. Pat. No. 4,681,893 to B. D. Roth pertains to trans-6[2-(3-or 4-carboxamido-substituted pyrrol-1-yl)alkyl]-4-hydroxypyran-2-ones useful as hypochloesterolemic agents.

U.S. Pat. No. 4,668,699 to Hoffman et al. discloses semi-synthetic analogs of compactin and mevinolin and the dihydro and tetrahydro analogs thereof for antihypercholesterolemic application.

U.S. Pat. No. 4,282,155 to Smith et al. is directed to 6(R)-[2-(8'-Etherified-hydroxy-2',6'-dimethylpolyhydronaphtyl1')ethyl]-4(R)-hydroxy-3,4,5,6-tetrahydro-2H-pyran-2-ones for inhibition of biosynthesis of cholesterol.

U.S. Pat. No. 4,567,289 relates to methyl, ethyl, n-propyl, 2-(acetylamino)ethyl, or 1-(2,3-dihydroxy)propyl ester of E-(3R,5S)-7-(4'-fluoro-3,3',5-trimethyl[1,1'-biphenyl]-2-yl)3,5-dihydroxy-6-heptenoic acid that are HMG-CoA reductase inhibitors.

U.S. Pat. No. 4,611,067 discloses a process for the preparation of HMG-CoA reductase inhibitors which contain a 4-hydroxy-3,4,5,6-tetrahydro-2H-pyran-2-one moiety.

Germ. Offen. No. 3,817,375 disclosed HMG-CoA reductase inhibitors having the formula

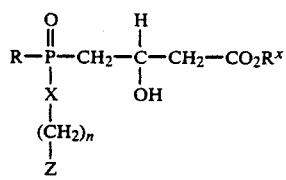

wherein:
R is OH, lower alkoxy or lower alkyl;
$R^x$ is H or alkyl;
X is H or —NH;
n is 1 or 2; and
Z is a hydropholic group.

Germ. Offen. No. 3,817,298 pertains to HMG-CoA reductase inhibitors having the formula

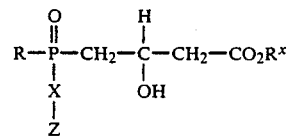

wherein:
R is OH or lower alkyl;
$R^x$ is H or alkyl;
X is —(CH2)a—, —CH=CH—, —C≡C— or —CH2O;
a is 1, 2 or 3; and
Z is a hydropholic group.

SUMMARY OF THE INVENTION

In accordance with the present invention, certain cyclohexenyl-phosphinyl-hydroxybutyrates and pharmaceutically acceptable salts thereof are provided which are potent inhibitors of HMG-CoA reductase. Specifically, the invention provides compounds of the formula:

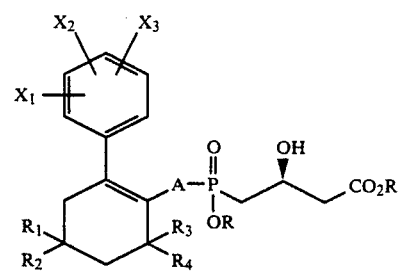

wherein
A is:
—C≡C—,
—CH=CH or
—(CH$_2$)$_m$;
$X_1$, $X_2$ and $X_3$ are independently:
H,
$C_1$–$C_6$ alkyl,
halogen,
NRR,
aryl,
$CF_3$
$SO_nR$,
OR or
RO(CH$_2$)$_m$;
R, $R_1$, $R_2$, $R_3$ and $R_4$ are independently:
H or
$C_1$–$C_6$ alkyl; and
n is 0, 1 or 2;
m is 1, 2, 3; and
pharmaceutically acceptable salts thereof.

DETAILED DESCRIPTION OF THE INVENTION

As employed above and throughout the specification, the following terms, unless otherwise indicated, shall be understood to have the following meaning:

"Alkyl" means a saturated or unsaturated aliphatic hydrocarbon which may be either straight- or branched-chained containing from about one to about six carbon atoms.

"Aryl" means an aromatic hydrocarbon radical having 6 to 10 carbon atoms. The preferred aryl groups are phenyl, substituted phenyl and naphthyl. The term "substituted" means "alkyl" substitution.

"Halogen" means Cl, F, Br and I.

The pharmaceutically acceptable salts of the present invention include those formed from sodium, potassium, calcium, aluminum, lithium, magnesium, zinc, lysine, arginine, procaine, ethylenediamine and piperazine.

The invention encompasses optical and stereoisomers of the compounds and mixtures thereof defined by the structural formula.

The general procedure for producing the compounds of the present invention are shown in Schemes I, II and III.

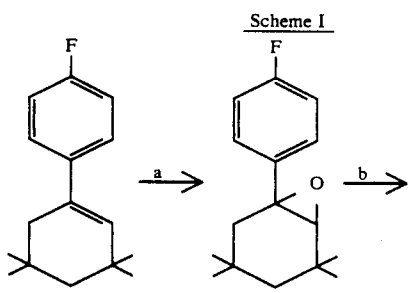

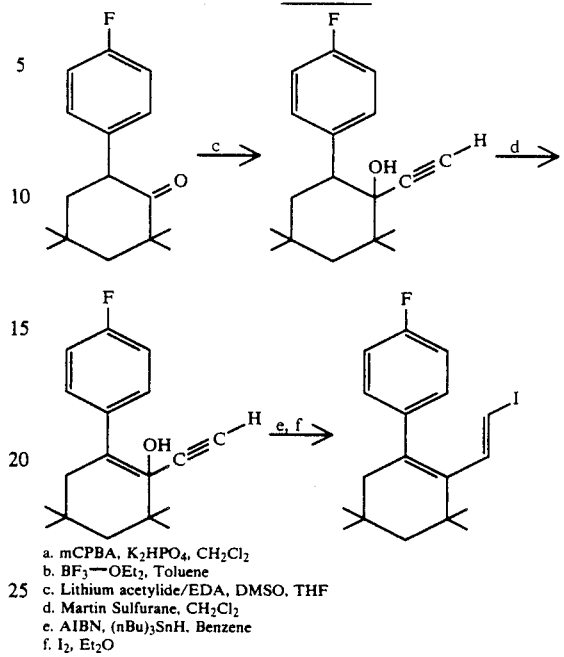

a. mCPBA, K₂HPO₄, CH₂Cl₂
b. BF₃—OEt₂, Toluene
c. Lithium acetylide/EDA, DMSO, THF
d. Martin Sulfurane, CH₂Cl₂
e. AIBN, (nBu)₃SnH, Benzene
f. I₂, Et₂O

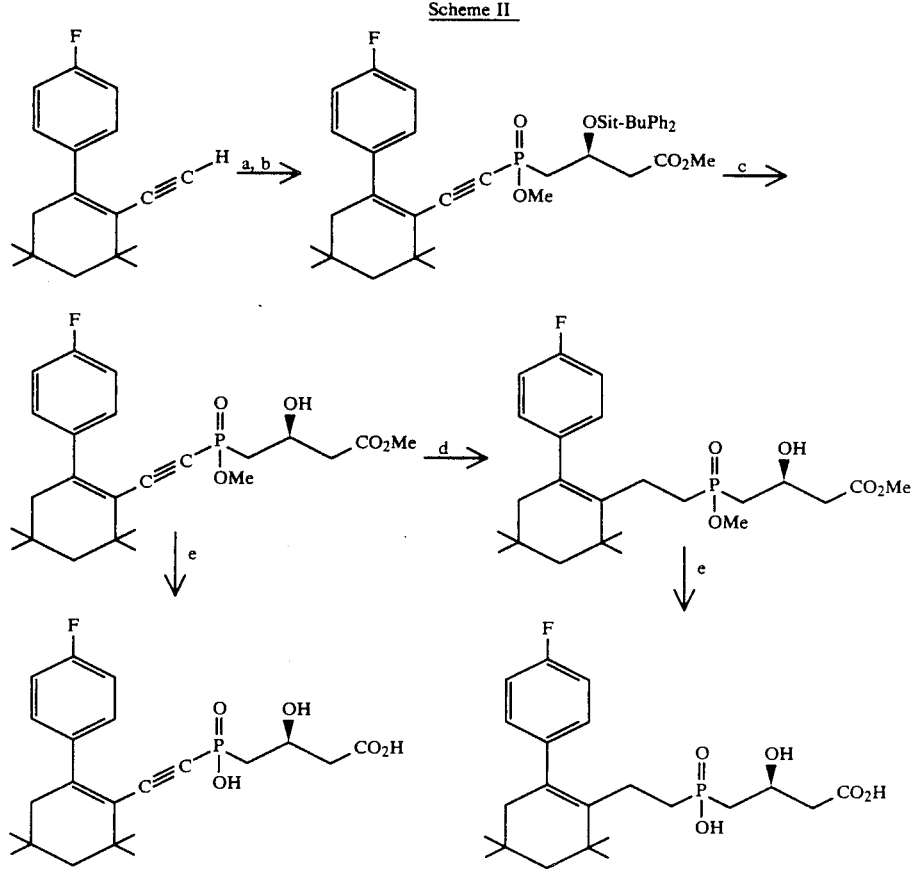

a. nBuLi, THF, −78° C.
b. methyl 4-(methylchlorophosphinyl)-3-(t-butyldiphenylsilyloxy)butyrate
c. Acetic acid, tetrabutylammonium fluoride
d. Pd/C, H₂, ethyl acetate, 10 psi.
e. LiOH, THF—MeOH—H₂O

Scheme III

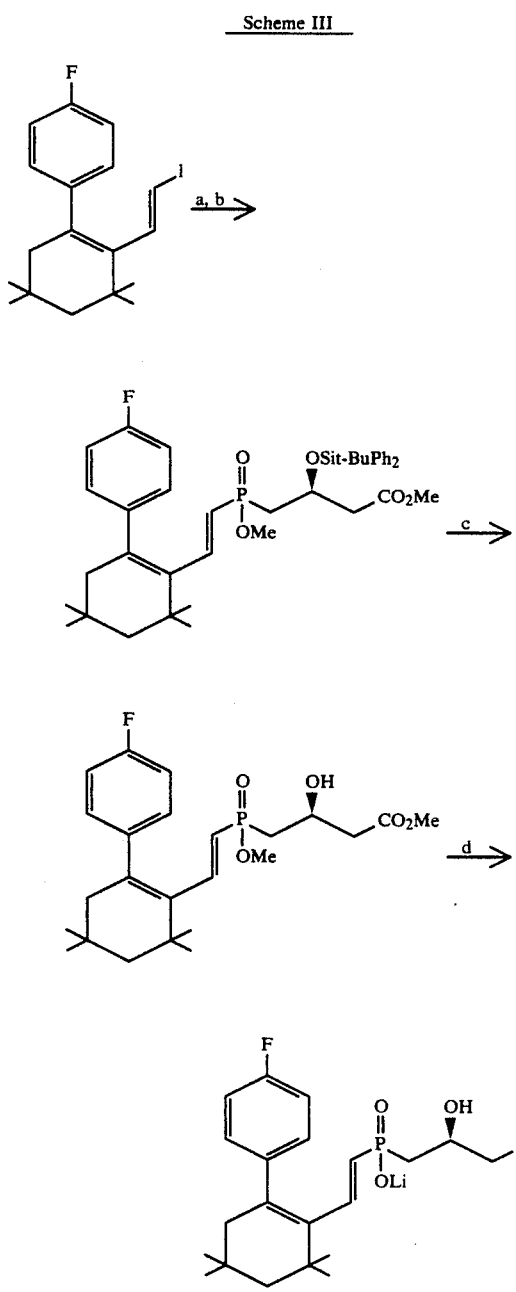

a. nBuLi, THF, −78° C.

b. methyl 4-(methylchlorophosphinyl)-3-(t-butyldiphenylsilyloxy)butyrate c. Acetic acid, tetrabutylammonium fluoride d. LiOH, THF—MeOH—H₂O The starting materials were obtained from the Aldrich Chemical Co. but they may also be synthesized in accordance with methods known in the art.

The following preparative examples will further illustrate the invention.

EXAMPLE 1

A.

2-[4-Fluorophenyl]-4,4,6,6-tetramethyl-1,2-epoxycyclohexane

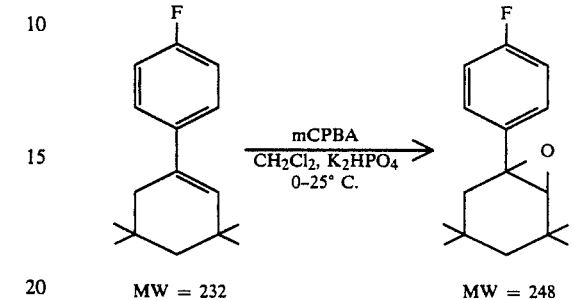

To a cooled solution (0°C.) of 20 g (0.086 mol) 2-[4fluorophenyl]-4,4,6,6tetramethylcyclohexene and 27.6 g (0.12 mol) $K_2HPO_4$ in 500 ml $CH_2Cl_2$ was added a solution of 26 g (0.12 mol) mCPBA in 500 ml $CH_2Cl_2$. The resulting milky solution was allowed to warm to room temperature and stirred overnight, filtered, washed with cold 5% aqueous NaOH and $H_2O$, dried and concentrated in vacuo to afford the desired epoxide. This material is of sufficient purity to be used in the next step.

B.

2-[4-Fluorophenyl]-4,4,6,6-tetramethylcyclohexanone

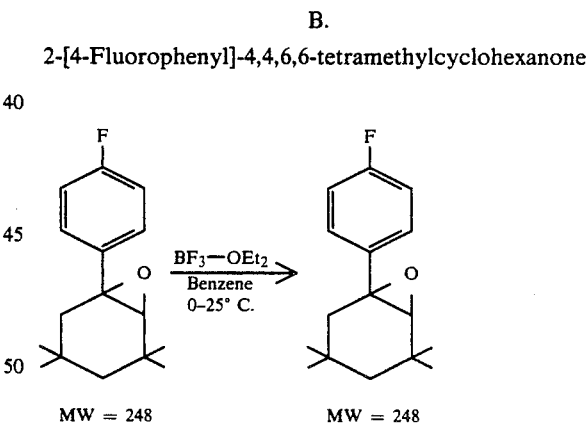

To a cooled solution (0° C.) of 21.3 g (0.08 mol) epoxide obtained in Example 1A in benzene (200 ml) was slowly added 5 ml (0.04 mol) $BF_3 \cdot OEt_2$. The resulting solution was warmed to 25° C. and allowed to stir for 2 hours at 25° C. The mixture was diluted to twice the volume with ether and washed with aqueous saturated $NH_4^+Cl^-$ and $H_2O$. The mixture was dried and concentrated in vacuo to provide an oily residue. The residue was taken up in hot pentane and cooled and the crystalline ketone (m.p. 64°–65° C.) was collected by filtration.

C. 1-Ethynyl-2-[4-fluorophenyl]-4,4,6,6-tetramethylcyclohexanol

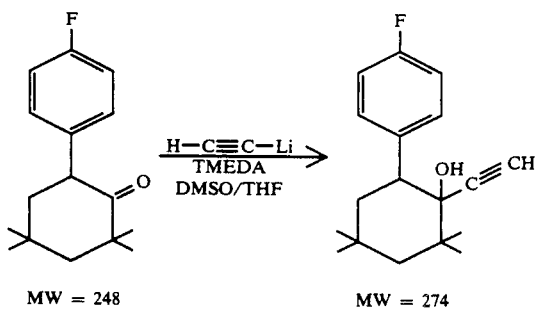

MW = 248    MW = 274

To a solution of 2.8 g (30.2 mmol) lithium acetylide/EDA complex in 6 ml DMSO/THF (5/1) was added a solution of 5g (20 mmol) ketone obtained in Example 1B, in 4 ml THF. The solution was stirred for 14 hours, diluted with ether and washed with saturated aqueous $NH_4^+Cl^-$, $H_2O$ and dried. Concentration in vacuo and purification on silica gel with 1:1 hexane:$CHCl_3$ provided the hydroxy acetylene.

D. 1-Ethynyl-2-[4-fluorophenyl]-4,4.6,6-tetramethylcyclohexene

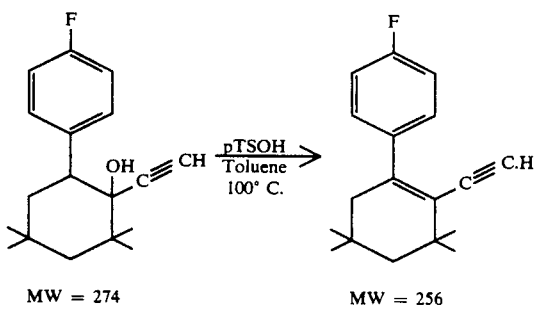

MW = 274    MW = 256

5 g (18.2 mmol) of the hydroxy acetylene obtained in Example 1D was taken up in methylene chloride (50 ml) and treated with 12.3 g (18.2 mmol) Martin Sulfurane (Aldrich Chemical Co.). The solution was allowed to stir for 3 hours, washed with cold 10% sodium hydroxide and $H_2O$. The solution was dried and concentrated to provide an oily residue. Purification by silica gel chromatography with hexane provided the title compound.

E. Methyl (S)-4-[[2-[4-fluorophenyl]4,4,6,6-tetramethylcyclohexenylethenyl-]methoxyphosphinyl]-3-tert-butyldiphenyl silyloxybutyrate

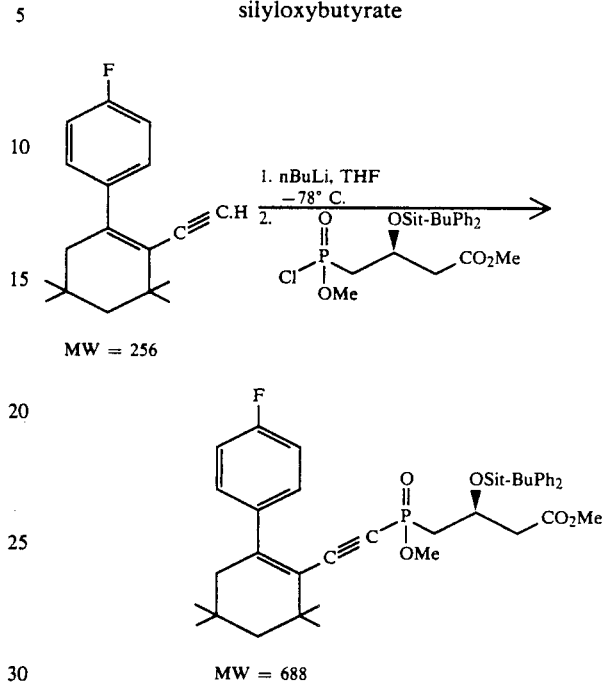

MW = 256

MW = 688

To a solution of 5 g (19.5 mmol) the above acetylene in THF (50 ml) at −78° C. was added 7.8 ml (19.5 mmol) nBuLi (2.5M in hexane). The resulting yellow solution was warmed to 0° C. for 3 hours then cooled to −78° C. and treated with a solution of 8.5 g (19.5 mmol) methyl (S)-4-(chloromethoxyphosphinyl)-3-tert-butyldiphenylsiloxy)butyrate in THF (5 ml). This solution was allowed to stir for 2 hours at −78° C. and quenched with saturated aqueous $NH_4^+Cl^-$. Extraction with ethyl acetate, drying and concentration in vacuo provided the desired coupled product. This material was purified by silica gel chromatography with hexane:ethyl acetate. Methyl (S)-4-(chloromethoxyphosphinyl)-3-(tert-butyldiphenylsiloxy)butyrate can be made, inter alia, by the method described in $E_1$ through $E_8$.

$E_1$ Methyl [S-(R*, S*)]-2,4-dibromo-3hydroxybutyrate

A solution of [R-(R*,R*)]-2,3,4-trihydroxybutanoic acid calcium salt, hydrate (24.0 g) in 30–32% HBr in acetic acid (170 ml) was stirred at room temperature for 20 hours and methanol (800 ml) was added. The mixture was stirred overnight and the volatiles removed in vacuo. Purification of the residue by distillation provided the oily product.

$E_2$ Methyl (S)-4-bromo-3-hydroxybutyrate

A mixture of methyl [S-(R*,S*)]-2,4-dibromo-3-hydroxybutyrate (7.0 g), and anhydrous sodium acetate (7.0 g), 5% palladium on carbon (450 mg) in 70 ml ethyl acetate and 7 ml acetic acid was hydrogenated at 1 atm. $H_2$ for approximately 2 hours and filtered over celite. The filtrate was washed with saturated $NaHCO_3$, $H_2O$ and brine and dried ($MgSO_4$). Removal of the volatiles in vacuo provided a residue which was purified by vacuum distillation and gave the product as a clear oil.

E₃ Methyl (S)-4-bromo-3-(tert-butyldiphenylsiloxy)butyrate

To a solution of the product obtained in E₂ (6.5 g, 33.1 mmol), imidazole (11.3 g, 165.5 mmol) and 4-dimethylaminopyridine (20 mg) in anhydrous DMF was added dropwise t-butyldiphenylsilyl chloride (9.49 ml, 36.4 mmol). The mixture was kept at room temperature overnight, diluted with ethyl acetate and H₂O. The organic layer was washed with H₂O, 10% KHSO₄, and brine and dried (MgSO₄). Removal of the volatiles in vacuo provided the oily product which was used without further purification.

E₄ Methyl (S)-4-iodo-3-(tert-butyldiphenylsiloxy)butyrate

A mixture of the above produced bromide (6.33 g, 13.7 mmol) and sodium iodide (10.2 g, 68.3 mmol) in 50 ml anhydrous methyl ethyl ketone was heated at reflux for 5 hours, cooled to room temperature, diluted with ethyl acetate and filtered. The filtrate was washed with dilute NaHSO₄ and brine and dried (MgSO₄). Removal of the volatiles in vacuo provided a residue which was purified by HPLC using hexanes - ethyl acetate as the eluent. Concentration in vacuo of the product rich fractions provided the product as a pale yellow oil.

E₅ Methyl (S)-4-(diethoxyphosphinyl)-3-(tert-butyldiphenylsiloxy)butyrate

A mixture of the above produced iodide (5.5 g) and triethylphosphite (20 ml) was heated at 155° C. for 4 hours under an N₂ atmosphere. Removal of the excess triethylphosphite by vacuum distillation provided a residue which was purified by HPLC using hexanes - ethyl acetate as the eluent. Concentration in vacuo of the product rich fractions provided the product as a clear oil.

E₆ Methyl (S)-4-phosphono-3-(tert-butyldiphenylsiloxy)butyrate

To a solution of the above produced phosphonate (11.0 g, 22.4 mmol) in 60 ml anhydrous methylene chloride was added dropwise bis(trimethylsilyl)trifluoroacetamide (Aldrich Chemical Co.) (5.95 ml, 35.8 mmol) followed by the dropwise addition of trimethylsilyl bromide (Aldrich Chemical Co.) (7.39 ml, 56 mmol). The mixture was stirred at room temperature overnight, diluted with aqueous KHSO₄ and ethyl acetate. The organic layer was washed with brine and dried (MgSO₄). Removal of the volatiles in vacuo provided the phosphonic acid as an oil.

E₇ Methyl (S)-3(tert-butyldiphenylsiloxy)-4-(hydroxymethoxyphosphinyl)butyrate A mixture of the above produced phosphonic acid (14.8 mmol), dicyclohexylcarbodiimide (3.36 g, 16.3 mmol) and anhydrous methanol (1.2 ml, 29.6 mmol) in 20 ml anhydrous pyridine was stirred at room temperature overnight and the volatiles removed in vacuo. The residue was diluted with anhydrous toluene and the volatiles removed in vacuo. The residue was diluted with ethyl acetate and filtered. The filtrate was washed with aqueous HCl and brine and dried (MgSO₄). Removal of the volatiles in vacuo provided the oily product which was used without further purification.

E₈ Methyl (S)-4-(chloromethoxyphosphinyl)-3(tert-butyldiphenylsiloxy)butyrate To the above produced phosphonic acid (4.35 g, 9.7 mmol) in 20 ml anhydrous methylene chloride was added dropwise trimethylsilyldiethylamine (3.69 ml, 19.4 mmol). The mixture was stirred 90 minutes and the volatiles removed in vacuo. The residue was diluted with anhydrous toluene and the volatiles removed in vacuo. To the residue in 30 ml methylene chloride and DMF (2 drops) at −10° C. was added dropwise oxalyl chloride (0.93 ml, 10.7 mmol). The solution stirred 15 minutes, warmed to room temperature, stirred 60 minutes and the volatiles were removed in vacuo. The residue was diluted with toluene and the volatiles were removed in vacuo and provided the oily phosphonochloride which was used without further purification.

F. Methyl (S)-[4-[2-[4-fluorophenyl]-4,4,6,6-tetramethylcyclohexenylethenyl]methoxyphosphinyl]-3-hydroxybutyrate

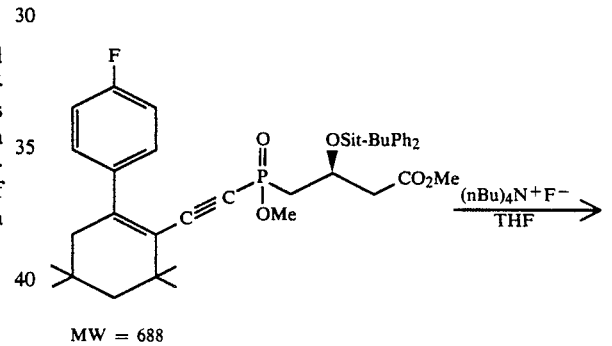

MW = 688

MW = 450

5 g (7.6 mmol) of the silyl ether produced in Example 1E was taken up in THF with 0.1 ml AcOH (1.7 mmol) and treated with 9.12 ml (9.12 mmol) of a 1M tetrabutylammonium fluoride solution in THF. This mixture was stirred at room temperature for 3 hours, quenched with 20% aqueous NaHCO₃ and extracted with ethyl acetate. The ethyl acetate layer was dried, concentrated in vacuo and purified on silica gel with hexane:ethyl acetate to provide the hydroxy-ester.

EXAMPLE 2

(S)-4[[2-[4-fluorophenyl]-4,4,6,6-tetramethylcyclohex-enylethenyl]hydroxyphosphinyl]-3-hydroxybutyrate dilithium salt

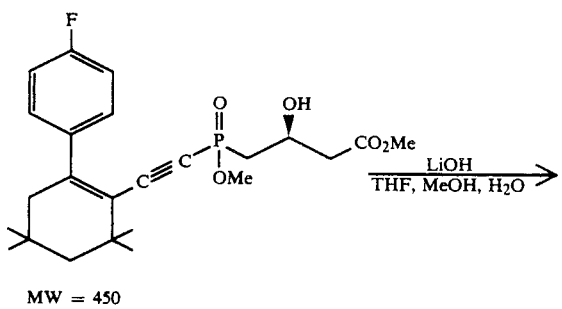

5 g (11.9 mmol) of the hydroxy ester of Example 1F was dissolved in 10 ml THF·MeOH·H$_{20}$ (7.2 1) and treated with 0.57 g (23.9 mmol) LiOH. The solution was concentrated in vacuo to provide the desired dilithium salt.

EXAMPLE 3

Methyl (S)-4-[[2-[2-[4-fluorophenyl]-4,4,6,6-tetramethylcyclohexenyl]ethyl]methoxyphosphinyl]-3-hydroxybutyrate

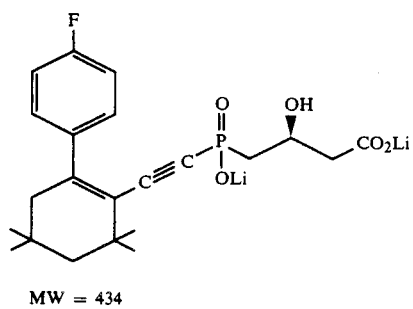

A solution of 5 g (11.9 mmol) hydroxy ester of Example 1F in ethyl acetate with 0.5 g (10% by wt.) Pd/C was hydrogenated under 10 psi for 4 hours. Filtration, concentration and purification by silica gel chromatography provide the saturated phosphinyl butyrate.

EXAMPLE 4

(S)-4-[[2-[2-[4-fluorophenyl]-4,4,6,6-tetramethylcyclohexenyl]ethyl]hydroxyphosphiny]-3-hydroxy butyrate dilithium salt

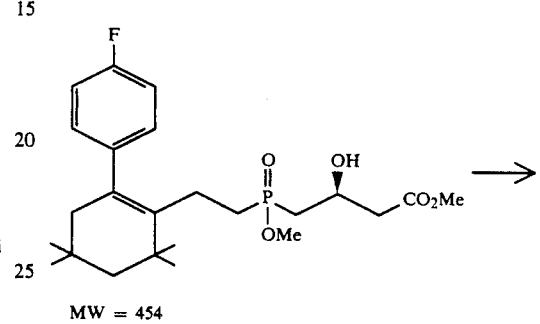

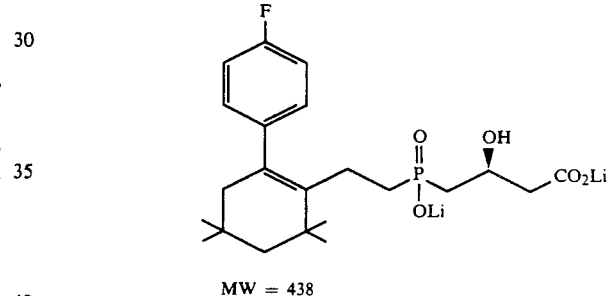

5 g (11.8 mmol) of the saturated hydroxy ester of Example 3 was dissolved in 10 ml THF·MeOH·H$_2$O (7.2 1) and treated with 0.57 g (23.6 mmol) LiOH. The solution was concentrated in vacuo to provide the desired saturated phosphinyl butyrate as the dilithium salt.

EXAMPLE 5

A.

1-[2-Iodoethenyl]-2-[4-fluorophenyl]-4,4,6,6-tetramethylcyclohexene

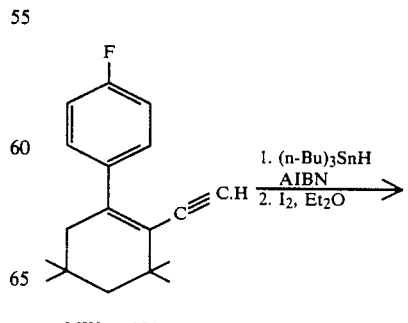

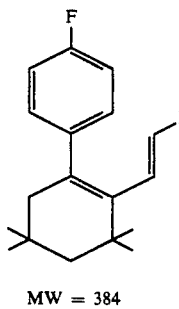

MW = 384

5 g (19.5 mmol) of the acetylene produced in Example 4 was added to a solution of 17.0 g (58.5 mmol) (nBu)₃SnH and 3.2 g (1.95 mmol) AIBN in benzene. The solution was warmed to 75° C. and maintained for 5 hours, cooled to room temperature and then added to a solution of I₂ in ether. This mixture was quenched with sodium metabisulfite solution (20%), extracted with ether, dried and concentrated to yield, after silica gel chromatography with hexane, the desired trans-iodo olefin.

B. Methyl (S)-4-[[2-[2-[4-fluorophenyl[-4,4,6,6-tetramethylcyclohexenyl]ethenyl]methoxyphosphinyl]-3-tert-butyldiphenylsilyloxybutyrate

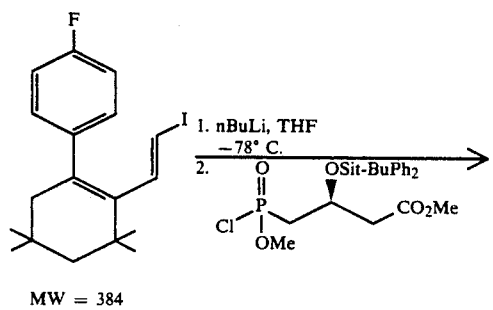

MW = 384

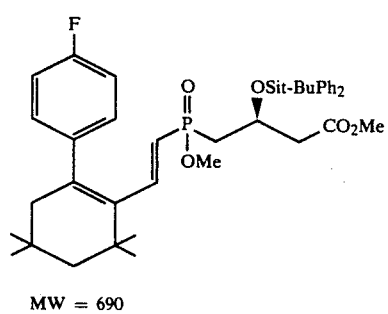

MW = 690

To a −78° C. solution of 5 g (13.0 mmol) trans-iodo olefin produced in Example 5A in THF was added 5.2 ml (13.0 mmol) n-BuLi (2.5M in hexane). The resulting solution was stirred for 2 hours then treated with 5.7g (13.0 mmol) methyl 4-(methylchlorophosphinyl)-3-(t-butyldiphenylsilyloxy)butyrate in 5 ml THF. This solution was stirred for 3 hours then quenched with saturated aqueous NH₄⁺Cl⁻ and extracted with ethyl acetate. The ethyl acetate layer was dried, concentrated in vacuo and provided crude trans alkenyl phosphinylbutyrate which was used without purification.

C. Methyl (S)-4-[[2-[2-[4-fluorophenyl]-4,4,6,6-tetramethylcyclohexenyl]ethenyl]methoxyphosphinyl]-3-hydroxybutyrate

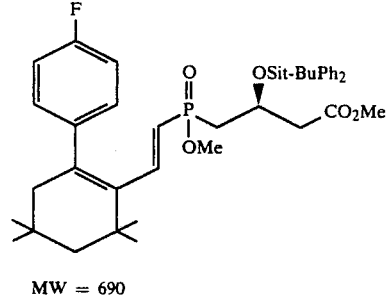

MW = 690

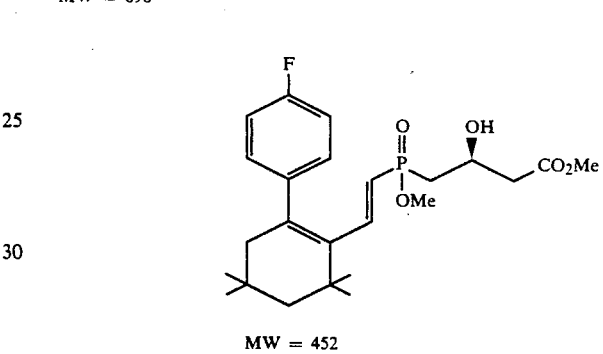

MW = 452

5 g (7.5 mmol) of the trans-alkenyl silyl ether produced in Example 5B in 5 ml THF was treated with 0.1 ml(1.7 mmol) AcOH, then 9.0 ml (9.0 mmol) IN tetrabutylammonium fluoride in THF. This mixture was stirred at room temperature, then quenched with 20% aqueous NaHCO₃, extracted with ethyl acetate, dried and concentrated in vacuo to provide, after silica gel chromatography, the hydroxy ester.

EXAMPLE 6

(S)-4-[[2-[2-[4-fluorophenyl]-4,4,6,6-tetramethylcyclohexenyl]ethenyl]hydroxyphosphinyl]-3-hydroxybutyrate dilithium salt

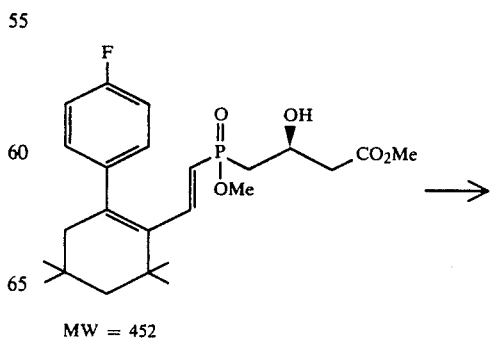

MW = 452

-continued

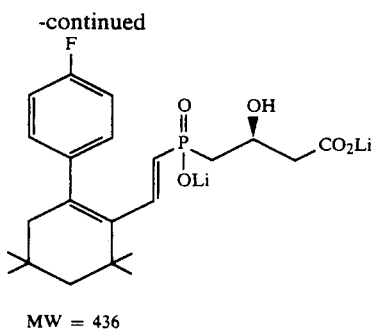

MW = 436

5.0 g (11.9 mmol) of a solution of trans diene ester of Example 5C, in 10 ml THF·MeOH·H$_2$O (7.2 1), was treated with 0.57 g (23.8 mmol) LiOH. The solution was concentrated in vacuo to provide the desired dilithium salt.

Employing the general schemes detailed in Examples 1 through 6 the following compounds can be prepared:

(S)-4-[[2-[2-[3-methyl-4-fluorophenyl]-4,4,6,6-tetramethylcyclohexenyl]ethyl]hydroxyphosphinyl]-3-hydroxybutyrate dilithium salt;

(S)-4-[[2-[2-[3-methyl-4-fluorophenyl]-4,4,6,6-tetramethylcyclohexenyl]ethenyl]hydroxyphosphinyl]-3-hydroxybutyrate dilithium salt;

(S)-4-[[2-[3-methyl-4-fluorophenyl]-4,4,6,6-tetramethylcyclohexenyl]ethynylhydroxyphosphinyl]-3-hydroxybutyrate dilithium salt;

(S)-4-[[2-[2-[3-methyl-4-fluorophenyl]-4,4,6,6-tetraethylcyclohexenyl]ethyl]hydroxyphosphinyl]-3-hydroxybutyrate dilithium salt;

(S)-4-[[2-[2-[3-methyl-4-fluorophenyl]-4,4,6,6-tetraethylcyclohexenyl]ethenyl]hydroxyphosphinyl]-3-hydroxybutyrate dilithium salt;

(S)-4-[[2-[3-methyl-4-fluorophenyl]-4,4,6,6-tetramethylcyclohexenyl]ethynylhydroxyphosphinyl]-3-hydroxybutyrate dilithium salt;

(S)-4-[[2-[2-[3,4-dichlorophenyl]-6,6-dimethylcyclohexenyl]ethyl]hydroxyphosphinyl]-3-hydroxybutyrate dilithium salt;

(S)-4-[[2-[3-fluoro-4-methoxyphenyl]-6,6-dimethylcyclohexenyl]ethynylhydroxyphosphinyl]-3-hydroxybutyrate dilithium salt;

(S)-4-[[2-[3-chloro-4-trifluoromethylphenyl]-6,6-dimethylcyclohexenyl]ethynylhydroxyphosphinyl]-3-hydroxybutyrate dilithium salt; and (S)-4-[[2-[3-hydroxymethyl-4-fluorophenyl]-4,4,6,6-tetramethylcyclohexenyl]ethynylhydroxyphosphinyl]-3-hydroxybutyrate dilithium salt.

The compounds of the present invention are useful as hypocholesterolemic or hypolipidemic agents by virtue of their ability to inhibit the biosynthesis of cholesterol through inhibition of the enzyme HMG-CoA reductase. Having such ability, the compounds are incorporated into pharmaceutically acceptable carriers and administered to a patient in need of such cholesterol biosynthesis inhibition orally or parenterally. Such pharmaceutical formulations to contain at least one compound according to the invention.

Suitable carriers include diluents or fillers, sterile aqueous media and various non-toxic organic solvents. The compositions may be formulated in the form of tablets, capsules, lozenges, trochees, hard candies, powders, aqueous suspensions, or solutions, injectable solutions, elixirs, syrups and the like and may contain one or more agents selected from the group including sweetening agents, flavoring agents, coloring agents and preserving agents, in order to provide a pharmaceutically acceptable preparation.

The particular carrier and the ratio of active compound to carrier are determined by the solubility and chemical properties of the compounds, the particular mode of administration and standard pharmaceutical practice. For example, excipients such as lactose, sodium citrate, calcium carbonate and dicalcium phosphate and various disintegrants such as starch, alginic acid and certain complex silicates, together with lubricating agents such as magnesium stearate, sodium lauryl sulfate and talc, can be used in producing tablets. For a capsule form, lactose and high molecular weight polyethylene glycols are among the preferred pharmaceutically acceptable carriers.

Where aqueous suspensions for oral use are formulated, the carrier can be emulsifying or suspending agents. Diluents such as ethanol, propylene glycol, and glycerin and their combinations can be employed as well as other materials.

For parenteral administration, solutions or suspensions of these compounds in aqueous alcoholic media or in sesame or peanut oil or aqueous solutions of the soluble pharmaceutically acceptable salves can be employed.

The dosage regimen in carrying out the methods of this invention is that which insures maximum therapeutic response until improvement is obtained and thereafter the minimum effective level which gives relief. Doses may vary, depending on the age, severity, body weight and other conditions of the patients but are ordinarily in the area of 5 mg/kg to 500 mg/kg of body weight in oral administration; such may, of course be given in two to four divided doses. With other forms of administration equivalent or adjusted doses will be administered depending on the route of administration.

Compounds of the present invention were found to exhibit hypocholesterolemic and hypolipidemic activity as measured by the HMGR Screen method which follows. Male rats were acclimated to an alternate 12 hour light-dark cycle for a period of 2–3 weeks. The animals, weighing 180–230 g, were fed ad libitum a rat chow containing 2% cholestyramine for 5 days prior to sacrifice at the mid-dark period. Liver microsomes were prepared and HMGR enzyme was solubilized from the microsomes by freeze-thaw manipulation in high ionic strength buffer. The enzyme preparation was stored at −80° C. in 300 μl portion samples. Prior to use, the enzyme was activated at 37° C. for 30 minutes in a reaction mixture. The reaction mixture contained in a volume of 240 μl : 0.14M potassium phosphate buffer (pH 7.0); 0.18M KCl; 3.5 mM EDTA; 10 mM dithiothreitol; 0.1 mg/ml BSA; 30,000 cpm of [$^{14}$C] HMG-CoA; 20 μM HMG-CoA, and 200 μg of solubilized enzyme with and without inhibitors (in 10 μl DMSO). After 5 minutes incubation at 37° C. the reaction was initiated with 0.2 mM NADPH. The final assay volume was 300 μl. The reaction then was terminated with 100 μl of 1N HCl. After an additional incubation for 15 minutes at 37° C. to allow for complete lactonization of the product, the mixture was diluted with 3 ml GDW. The diluted mixture was then poured over a 0.7×1.4 cm column containing 100–200 mesh Bio-Rex ion-exchange resin (chloride form of Bio-Rad) which was equilibrated with distilled water. With this resin the unreacted [$^{14}$C] HMG-CoA was adsorbed and the product [$^{14}$C] lactone was eluted (80% recovery) directly into scintillation vials. After the addition of 10 ml of Aquasol ®, radioactivities of the samples were measured in a scintillation counter.

What is claimed is:
1. A compound of the formula

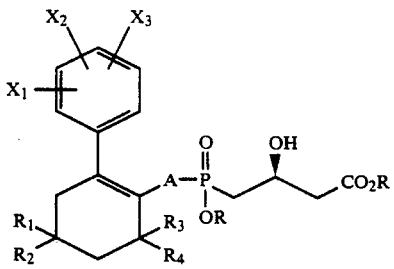

wherein
A is:
—C≡C—,
—CH=CH or
—(CH$_2$)$_m$;
$X_1$, $X_2$ and $X_3$ are independently:
H,
$C_1$–$C_6$ alkyl,
halogen,
NRR,
aryl,
$CF_3$
$SO_nR$,
OR or
$RO(CH_2)_m$;
R, $R_1$, $R_2$, $R_3$ and $R_4$ are independently:
H or
$C_1$–$C_6$ alkyl; and
n is 0, 1 or 2;
m is 1, 2, 3; and
pharmaceutically acceptable salts thereof.

2. The compound of claim 1 wherein $X_1$ is phenyl.
3. The compound of claim 1 wherein $X_1$ is alkyl substituted phenyl.
4. The compound of claim 1 wherein is $X_2$ naphthyl.
5. The compound of claim 1 wherein $X_2$ is alkyl substituted naphthyl.
6. The compound of claim 1 wherein $X_3$ is F.
7. The compound of claim 1 wherein:
A is —C≡C—;
$X_1$ and $X_2$ are H;
$X_3$ is F;
R, $R_1$, $R_2$ and $R_3$ are H; and
$R_4$ is $C_1$–$C_6$ alkyl.
8. Methyl (S)-4-[[2-[4-fluorophenyl]-4,4,6,6-tetramethylcyclohexenylethenyl]methoxyphosphinyl]-3-hydroxybutyrate.
9. (S)-4-[[2-[4-fluorophenyl]-4,4,6,6-tetramethylcyclohexenylethynyl]hydroxyphosphinyl]-3-hydroxybutyrate dilithium salt.
10. Methyl (S)-4-[[2-[2-[4-fluorophenyl]-4,4,6,6-tetramethylcyclohexenyl]ethyl]methoxyphosphinyl]-3-hydroxybutyrate.
11. (S)-4-[[2-2-[4-fluorophenyl]-4,4,6,6-tetramethylcyclohexenyl]ethyl]hydroxyphosphinyl]-3-hydroxybutyrate dilithium salt.
12. Methyl (S)-4-[[2-[2-[4-fluorophenyl]-4,4,6,6-tetramethylcyclohexenyl]ethenyl]methoxyphosphinyl]-3-hydroxybutyrate.
13. (S)-4-[[2-[2-[4-fluorophenyl]-4,4,6,6-tetramethylcyclohexenyl]ethenyl]hydroxyphosphinyl]-3-hydroxybutyrate dilithium salt.
14. A hypocholesterolemic, hypolipidemic pharmaceutical composition comprising a therapeutically effective amount of a compound of claim 1 and a pharmaceutically acceptable carrier.
15. The hypocholesterolemic, hypolipidemic pharmaceutical composition of claim 14 wherein said compound is selected from the group consisting of:
Methyl (S)-4-[[2-[4-fluorophenyl]-4,4,6,6-tetramethylcyclohexenylethenyl]methoxyphosphinyl]-3-hydroxybutyrate;
(S)-4-[[2-[4-fluorophenyl]-4,4,6,6-tetramethylcyclohexenylethynyl]hydroxyphosphinyl]-3-hydroxybutyrate dilithium salt; and
Methyl (S)-4-[[2-[2-[4-fluorophenyl]-4,4,6,6-tetramethylcyclohexenyl]ethyl]methoxyphosphinyl]-3-hydroxybutyrate.
16. The hypocholesterolemic, hypolipidemic pharmaceutical composition of claim 14 wherein said compound is selected from the group consisting of:
(S)-4-[[2-2-[4-fluorophenyl]-4,4,6,6-tetramethylcyclohexenyl]ethyl]hydroxyphosphinyl]-3-hydroxybutyrate dilithium salt;
Methyl (S)-4-[[2-[2-[4-fluorophenyl]-4,4,6,6-tetramethylcyclohexenyl]ethenyl]methoxyphosphinyl]-3-hydroxybutyrate; and
(S)-4-[[2-[2-[4-fluorophenyl]-4,4,6,6-tetramethylcyclohexenyl]ethenyl]hydroxyphosphinyl]-3-hydroxybutyrate dilithium salt.
17. The hypocholesterolemic, hypolipidemic pharmaceutical composition of claim 14 wherein said compound is selected from the group consisting of:
(S)-4-[[2-[2-[3-methyl-4-fluorophenyl]-4,4,6,6-tetramethylcyclohexenyl]ethyl]hydroxyphosphinyl]-3-hydroxybutyrate dilithium salt;
(S)-4-[[2-[2-[3-methyl-4-fluorophenyl]-4,4,6,6-tetramethylcyclohexenyl]ethenyl]hydroxyphosphinyl]-3-hydroxybutyrate dilithium salt;
(S)-4-[[2-[3-methyl-4-fluorophenyl]-4,4,6,6-tetramethylcyclohexenyl]ethynylhydroxyphosphinyl]-3-hydroxybutyrate dilithium salt;
(S)-4-[[2-[2-[3-methyl-4-fluorophenyl]-4,4,6,6-tetraethylcyclohexenyl]ethyl]hydroxyphosphinyl]-3-hydroxybutyrate dilithium salt; and
(S)-4-[[2-[2-[3-methyl-4-fluorophenyl]-4,4,6,6-tetraethylcyclohexenyl]ethenyl]hydroxyphosphinyl]-3-hydroxybutyrate dilithium salt.
18. The hypocholesterolemic, hypolipidemic pharmaceutical composition of claim 14 wherein said compound is selected from the group consisting of:
(S)-4-[[2-[3-methyl-4-fluorophenyl]-4,4,6,6-tetramethylcyclohexenyl]ethynylhydroxyphosphinyl]-3-hydroxybutyrate dilithium salt;
(S)-4-[[2-[2-[3,4-dichlorophenyl]-6,6-dimethylcyclohexenyl]ethyl]hydroxyphosphinyl]-3-hydroxybutyrate dilithium salt;
(S)-4-[[2-[3-fluoro-4-methoxyphenyl]-6,6-dimethylcyclohexenyl]ethynylhydroxyphosphinyl]-3-hydroxybutyrate dilithium salt;
(S)-4-[[2-[3-chloro-4-trifluoromethylphenyl]-6,6-dimethylcyclohexenyl]ethynylhydroxyphosphinyl]-3-hydroxybutyrate dilithium salt; and
(S)-4-[[2-[3-hydroxymethyl-4-fluorophenyl]-4,4,6,6-tetramethylcyclohexenyl]ethynylhydroxyphosphinyl]-3-hydroxybutyrate dilithium salt.
19. A method of inhibiting cholesterol biosynthesis in a patient in need of such treatment comprising administering a pharmaceutical composition defined in claim 14.

* * * * *